United States Patent
Venge

(10) Patent No.: US 9,476,880 B2
(45) Date of Patent: Oct. 25, 2016

(54) METHODS, DEVICES AND KITS FOR DETECTING OR MONITORING ACUTE KIDNEY INJURY

(75) Inventor: Per Venge, Uppsala (SE)

(73) Assignee: FUTURE MEDICAL DIAGNOSTICS CO., LTD., Suzhou, Jiangsu Province (CN)

( * ) Notice: Subject to any disclaimer, the term of this patent is extended or adjusted under 35 U.S.C. 154(b) by 999 days.

(21) Appl. No.: 13/130,456

(22) PCT Filed: Nov. 23, 2009

(86) PCT No.: PCT/IB2009/055299
§ 371 (c)(1),
(2), (4) Date: Aug. 8, 2011

(87) PCT Pub. No.: WO2010/058378
PCT Pub. Date: May 27, 2010

(65) Prior Publication Data
US 2011/0287455 A1   Nov. 24, 2011

Related U.S. Application Data

(60) Provisional application No. 61/116,713, filed on Nov. 21, 2008.

(51) Int. Cl.
*G01N 33/543* (2006.01)
*G01N 33/573* (2006.01)

(52) U.S. Cl.
CPC ....... *G01N 33/573* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 6,136,526 A | 10/2000 | Venge | |
| 7,056,702 B2* | 6/2006 | Villanueva et al. | 435/70.21 |
| 2004/0219603 A1 | 11/2004 | Devarajan et al. | |
| 2005/0272101 A1 | 12/2005 | Devarajan et al. | |
| 2007/0196876 A1* | 8/2007 | Moses et al. | 435/7.23 |
| 2007/0254370 A1 | 11/2007 | Devarajan et al. | |
| 2008/0014604 A1 | 1/2008 | Devarajan et al. | |
| 2008/0014644 A1 | 1/2008 | Barasch et al. | |
| 2008/0090304 A1 | 4/2008 | Barasch et al. | |
| 2010/0304413 A1* | 12/2010 | Uttenthal et al. | 435/7.94 |
| 2012/0142022 A1* | 6/2012 | Tu et al. | 435/7.1 |

FOREIGN PATENT DOCUMENTS

| | | |
|---|---|---|
| WO | 2004/088276 A2 | 10/2004 |
| WO | 2006/066587 A1 | 6/2006 |
| WO | 2009062520 A1 | 5/2009 |

OTHER PUBLICATIONS

Bennett et al., Urine NGAL Predicts Severity of Acute Kidney Injury After Cardiac Surgery: A prospective study, Clin J Am Soc Nephrol 3: Mar. 2008, pp. 665-673.*
Mishra et al, TheLancet.com, 365:1231-1238 (2005).
Kjeldsen et al, Journal of Immunological Methods, 198:155-164 (1996).
Zappitelli et al, Critical Care, 11(4):R84 (Aug. 2, 2007).
Cai, Clinica Chimica Acta, 4003:121-125 (Feb. 7, 2009).
Xu et al, Journal of Immunological Methods, 171:245-252 (1994).
Dent et al, Critical Care, 11(6):R127 (Dec. 10, 2007).
Yang et al, Molecular Cell, 10:1045-1056 (2002).
Bennett et al, Clin J Am Soc Nephrol, 3:665 (Mar. 12, 2008) (Abstract only).
Nickolas et al, Annals of Internal Medicine, 148(11):810-819 and W-180 (Jun. 3, 2008).
European Official Action, from corresponding EP Application No. 09 761 023.2 dated Jul. 27, 2012.
English Translation of Official Action and Search Report dated Jul. 22, 2014 from corresponding Chinese Application No. 200980155194.X, English portions only.

* cited by examiner

*Primary Examiner* — Gary W Counts
(74) *Attorney, Agent, or Firm* — Porter Wright Morris & Arthur LLP

(57) ABSTRACT

Methods for detecting acute kidney injury in an individual comprise (a) contacting a body fluid sample from the individual with an assay device including neutrophil gelatinase-associated lipocalin (NGAL) antibody and a detectable label, to allow complexing of NGAL protein in the sample with NGAL antibody, and determining an amount of complex formed between NGAL protein from the sample and NGAL antibody in the assay device using the detectable label, wherein NGAL antibody in the device has binding capacity with more than two NGAL protein epitopes, and wherein the amount of the formed complex represents a level of acute kidney injury. Methods for determining an origin of NGAL protein in a sample from an individual include the step of determining relative amounts of monomeric, dimeric and heterodimeric forms of NGAL protein in the sample and allow improved diagnosis and therefore better targeted treatment.

12 Claims, 11 Drawing Sheets

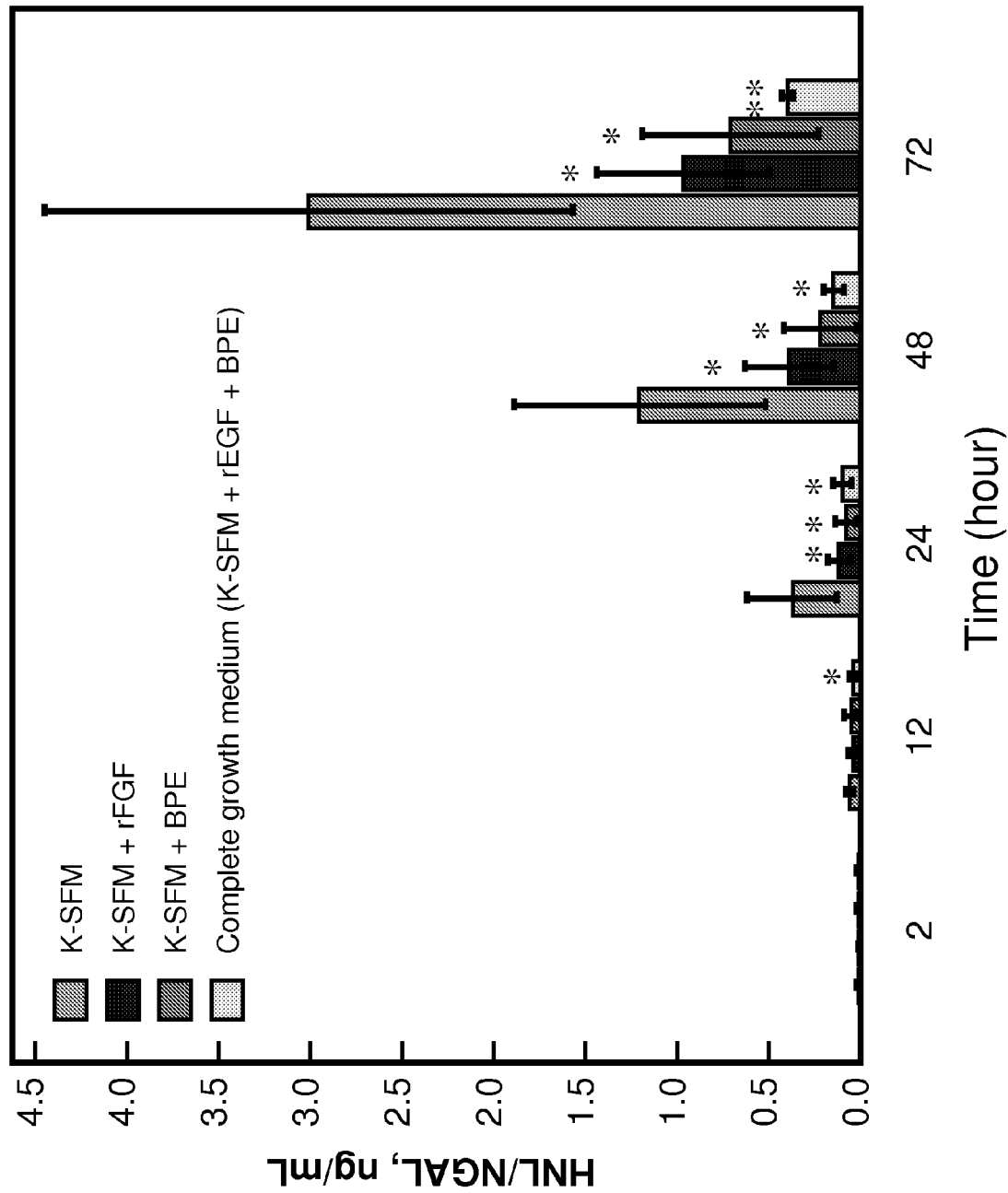

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer for NGAL

<400> SEQUENCE: 1
tcacctccgt cctgtttagc                                                      20

<210> SEQ ID NO 2
<211> LENGTH: 20
<212> TYPE: DNA
<213> ORGANISM: Artificial Sequence
<220> FEATURE:
<223> OTHER INFORMATION: Primer for NGAL

<400> SEQUENCE: 2
cgaagtcagc tccttggttc                                                      20

<210> SEQ ID NO 3
<211> LENGTH: 22
<212> TYPE: DNA
<213> ORGANISM: Artificial Sequence
<220> FEATURE:
<223> OTHER INFORMATION: Primer for Beta-actin

<400> SEQUENCE: 3
ttctacaatg agctgcgtgt gg                                                   22

<210> SEQ ID NO 4
<211> LENGTH: 23
<212> TYPE: DNA
<213> ORGANISM: Artificial Sequence
<220> FEATURE:
<223> OTHER INFORMATION: Primer for Beta-actin

<400> SEQUENCE: 4
gtgttgaagg tctcaaacat gat                                                  23
```

METHODS, DEVICES AND KITS FOR DETECTING OR MONITORING ACUTE KIDNEY INJURY

RELATED APPLICATIONS

The present application is a 371 of PCT/IB2009/055299 filed Nov. 23, 2009 and claims priority under 35 U.S.C. 119(e) of U.S. Application No. 61/116,713 filed Nov. 21, 2008.

FIELD OF THE INVENTION

The present invention is directed to methods, devices and kits for detecting or monitoring acute kidney injury, and particularly to such methods and kits which are based on measurement of neutrophil gelatinase-associated lipocalin (NGAL) protein, also known as human neutrophil lipocalin (HNL).

BACKGROUND OF THE INVENTION

Acute kidney injury (AKI) is a serious condition which can occur post-operatively, for example as a complication of cardiac surgery or kidney transplant, as a side effect from the in vivo introduction of diagnostic agents, for example, X-ray contrast agents, or nephrotoxic therapeutic agents, and the like, and/or in connection with other medical conditions, for example, diabetes, septicemia, hemorrhagic shock, and the like. As an example, acute kidney injury may occur in up to 30% of all patients undergoing cardiac surgery and is associated with a high mortality, a more complicated hospital course, dialysis dependency, diminished quality of life, and a higher risk for infectious complications. While the introduction of therapy in early stages of acute kidney failure has been shown to reduce the mortality rate and/or shorten treatment regimens, it has often been difficult to detect acute kidney failure in early stages.

In current clinical practice, the standard diagnosis of AKI is called RIFLE (Rise, Injury, Failure, Loss, End-stage renal disease) which is based on either the elevation of serum creatinine or urine output reduction. Serum creatinine is a reliable marker of general kidney function but it is an unreliable and delayed indicator during acute changes in kidney function. Fortunately, several promising novel biomarkers, including HNL/NGAL (hereafter referred to as NGAL), kidney injury molecule-1, cystatin C, and IL-18, have been discovered.

A great deal of attention has been directed to the use of NGAL protein as a marker for acute kidney injury. NGAL is a glycoprotein and was originally identified as a neutrophil specific granule component and a member of the lipocalin family of proteins. The protein was shown to exist both as a 25-kDa monomer and a 45-kDa disulfide-linked homodimer, and it may also be covalently complexed with neutrophil gelatinase (also known as matrix metalloproteinase 9, MMP-9) via an intermolecular disulphide bridge as a 135-kDa heterodimeric form. NGAL was first described as HNL as a specific marker of neutrophil activity in vivo and in vitro by Xu et al, *Journal of Immunological Methods*, 171:245-252 (1994), and for use as a diagnostic marker for inflammation by Venge, U.S. Pat. No. 6,136,526, which is incorporated herein by reference.

More recently, Devarajan et al, U.S. Patent Publications Nos. 2004/0219603 A1 and 2005/0272101 A1, disclose use of NGAL as a biomarker for renal tubular cell injury and other renal disease and injury. BioBorto Diagnostics, Gentofte, Denmark, recently offered an "NGAL ELISA Kit", for early diagnosis of acute renal failure, as well as mouse monoclonal anti-human NGAL antibody and mouse monoclonal anti-rat NGAL antibody. Additionally, Dent et al, *Critical Care*, 11(6):R127 (2007), describe the Triage® NGAL device from Biosite Inc., San Diego, Calif., employing an NGAL-specific monoclonal antibody conjugated to a fluorescent nanoparticle, for use in measuring NGAL as a biomarker of acute kidney injury.

However, further improvements in detecting and/or monitoring acute kidney injury are desired.

SUMMARY OF THE INVENTION

Accordingly, the present invention provides methods, devices and kits for detecting acute kidney injury and for monitoring the effectiveness of treatments for acute kidney injury.

In one embodiment, the invention is directed to a method for detecting acute kidney injury in an individual, comprising (a) contacting a body fluid sample from the individual with an assay device including neutrophil gelatinase-associated lipocalin (NGAL) antibody and a detectable label, to allow complexing of NGAL protein in the sample with NGAL antibody, and (b) determining an amount of complex formed between NGAL protein from the sample and NGAL antibody in the assay device using the detectable label, wherein NGAL antibody in the device has binding capacity with more than two NGAL protein epitopes, and wherein the amount of the formed complex represents a level of acute kidney injury.

In another embodiment, the invention is directed to a method for detecting acute kidney injury in an individual, comprising (a) contacting a body fluid sample from the individual with a polyclonal neutrophil gelatinase-associated lipocalin (NGAL) antibody, and (b) determining an amount of complex formed between NGAL from the sample and the polyclonal NGAL antibody using a detectable label, wherein the amount of the complex represents a level of acute kidney injury.

In an additional embodiment, the invention is directed to a method for monitoring the effectiveness of a treatment for acute kidney injury, comprising the steps of (a) contacting a first body fluid sample from the individual with a first assay device including neutrophil gelatinase-associated lipocalin (NGAL) antibody and a detectable label, to allow complexing of NGAL protein in the first sample with NGAL antibody, (b) determining an amount of complex formed between NGAL protein from the first sample and NGAL antibody in the first assay device using the detectable label, wherein NGAL antibody in the device has binding capacity with more than two NGAL protein epitopes, (c) contacting a second body fluid sample from the individual, obtained after commencing the treatment, with a second assay device including NGAL antibody and a detectable label, to allow complexing of NGAL protein in the second sample with NGAL antibody, (d) determining an amount of a second complex formed between NGAL from the second sample and the NGAL antibody in the second assay device using the detectable label, wherein NGAL antibody in the device has binding capacity with more than two NGAL protein epitopes, and (e) comparing the amount of the first complex with the amount of the second complex, wherein a decrease in the amount of the second complex as compared with the amount of the first complex indicates the treatment is effective.

In a further embodiment, the invention is directed to a method for monitoring the effectiveness of a treatment for acute kidney injury, comprising the steps of (a) contacting a first body fluid sample from the individual, obtained prior to the treatment, with a polyclonal neutrophil gelatinase-associated lipocalin (NGAL) antibody, (b) determining an amount of a first complex formed between NGAL protein from the first sample and the polyclonal NGAL antibody using a detectable label, (c) contacting a second body fluid sample from the individual, obtained after commencing the treatment, with a polyclonal NGAL antibody, (d) determining an amount of a second complex formed between NGAL from the second sample and the polyclonal NGAL antibody using a detectable label, and (e) comparing the amount of the first complex formed between NGAL from the first sample and the polyclonal NGAL antibody with the amount of the second complex formed between NGAL from the second sample and the polyclonal NGAL antibody, wherein a decrease in the amount of the second complex as compared with the amount of the first complex indicates the treatment is effective.

In yet a further embodiment, the invention is directed to a kit for detecting acute kidney injury in an individual. In one embodiment, the kit comprises an assay device including neutrophil gelatinase-associated lipocalin (NGAL) antibody and a detectable label adapted for use in determining an amount of complex formed between NGAL in a body fluid sample and NGAL antibody, wherein NGAL antibody in the device has binding capacity with more than two NGAL protein epitopes.

In another embodiment, the kit comprises a first polyclonal neutrophil gelatinase-associated lipocalin (NGAL) antibody adapted for contact with a body fluid sample, a second NGAL antibody adapted for use in determining an amount of complex formed between NGAL protein in a body fluid sample and the first polyclonal NGAL antibody, and a detectable label adapted for use in determining an amount of complex formed between NGAL in a body fluid sample and the first polyclonal NGAL antibody.

In a further embodiment, the invention is directed to an assay device for detecting acute kidney injury in an individual comprising a polyclonal NGAL antibody immobilized on a substrate and adapted for contact with a body fluid sample, and a detectable label adapted to bind to a complex of NGAL protein and the immobilized polyclonal NGAL antibody.

As these methods, devices and kits of the invention employ NGAL antibody having binding capacity with more than two NGAL protein epitopes, the methods and kits surprisingly exhibit improved sensitivity for NGAL as a biomarker and therefore exhibit improved sensitivity in detecting acute kidney injury. This improved sensitivity can provide earlier detection of such injury and consequently earlier therapeutic responses will be allowed.

In a further embodiment, the invention is directed to methods for determining an origin of neutrophil gelatinase-associated lipocalin (NGAL) protein in a sample from an individual. In a more specific embodiment, the methods may be used to distinguish between NGAL originating in the kidney and NGAL originating in neutrophils. In a one specific embodiment, such methods comprise (a) determining relative amounts of monomeric, dimeric and heterodimeric forms of NGAL protein in the sample, and (b) comparing the determined amounts, wherein a predominate amount of monomeric and/or heterodimeric NGAL protein as compared with dimeric NGAL protein indicates NGAL protein originating from the individual's kidney, while an equal or predominate amount of dimeric NGAL protein as compared with monomeric or heterodimeric NGAL protein indicates NGAL protein originating in the individual's neutrophils Determination or the origin of the NGAL protein will assist in condition diagnosis and will allow, inter alia, improved, targeted treatment.

These and additional advantages and improvements will be more fully understood in view of the following detailed description.

BRIEF DESCRIPTION OF THE DRAWINGS

The detailed description will be more fully understood in view of the drawings, in which:

FIG. 8 shows the time course of NGAL synthesis by HK-2 cells cultured in conditioned medium, determined at the indicated times, as described in Example 2. Values are means±SD from duplicate assays of three independent experiments. The markers * and ** represent $p<0.05$ and $p<0.01$, respectively.

Figure 1:
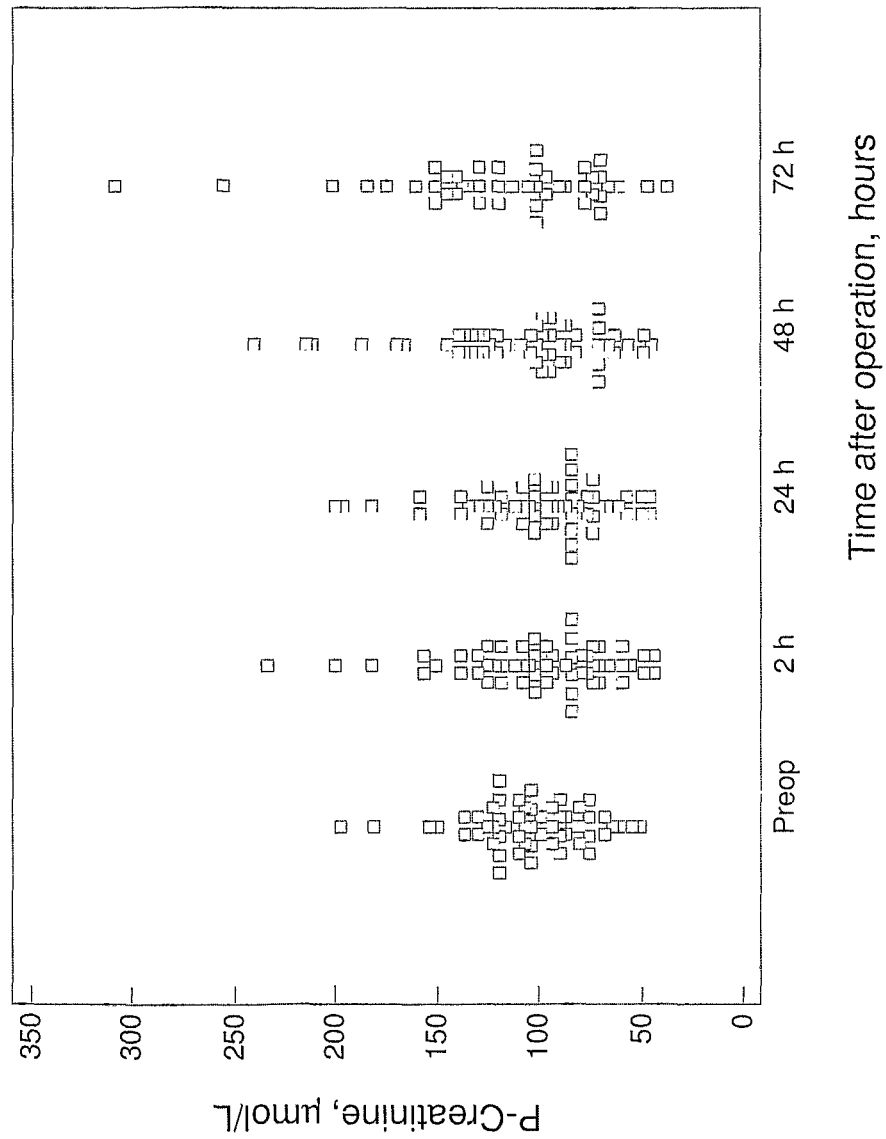
FIG. 1 shows pre- and post-operative levels of plasma creatinine as described in Example 1. Upper normal levels for men and women, respectively, are 100 µmol/L and 90 µmol/L. Pre-operative levels were significantly elevated as compared to the normal levels for both men and women ($p<0.001$).

The various aspects, features and embodiments of the invention will be more fully understood in view of the detailed description.

DETAILED DESCRIPTION

NGAL was originally isolated from human neutrophils and previous work indicated that the measurement of NGAL in blood is a superior means to distinguish acute infections caused by bacteria and virus. More recently, the close relationships between excretion of NGAL, for example in body fluid samples such as urine, and acute kidney injury has been studied. Surprisingly, a comparison of NGAL measurements with monoclonal-monoclonal assay and assays employing polyclonal antibody showed important differences in the clinical performance of these assays. The results evidenced that the choice of antibodies in the assays is critical and particularly the use of antibodies having the capability of reacting with more than two NGAL protein epitopes provide assays of increased sensitivity, evidencing that these assays identify different variants of NGAL excreted under various conditions. The present methods, devices and kits therefore employ NGAL antibody having the capability of reacting with more than two NGAL protein epitopes. In this regard, such NGAL antibody may comprise one or more polyclonal NGAL antibodies, and/or a combination of one or more polyclonal NGAL antibodies with one or more monoclonal NGAL antibodies, as described in further detail below. Further, the NGAL antibody or antibodies may be employed for capture of NGAL protein and/or with a detectable label.

The methods for detecting acute kidney injury in an individual may be applied for any human individual, and particularly for an individual who may be at risk for acute kidney injury. Such individuals include, but are not limited to those having cardiac surgery or kidney transplant, in vivo introduction of diagnostic agents, for example, X-ray contrast agents, or nephrotoxic therapeutic agents, and the like, and/or having diabetes, septicemia, hemorrhagic shock, or the like. In a specific embodiment, the individual is a cardiac surgery patient and the sample is obtained from the cardiac surgery patient within three hours of cardiac surgery. In an additional embodiment, the detection method is repeated on respective samples obtained at successively subsequent time periods after cardiac surgery, for example at 2 hours and 5 hours after surgery, at 2 hours and 12 hours after surgery, at 2 hours, 12 hours and 24 hours after surgery, or the like.

The methods employ a body fluid sample for detection. In a more specific embodiment, the sample comprises urine, blood, serum, or plasma, or a purified component thereof. In a more specific embodiment, the sample is urine.

In one embodiment, the method comprises (a) contacting a body fluid sample from the individual with an assay device including NGAL antibody and a detectable label, to allow complexing of NGAL protein in the sample with NGAL antibody, and (b) determining an amount of complex formed between NGAL protein from the sample and NGAL antibody in the assay device using the detectable label, wherein NGAL antibody in the device has binding capacity with more than two NGAL protein epitopes, and wherein the amount of the formed complex represents a level of acute kidney injury. As discussed above, NGAL antibody having binding capacity with more than two NGAL protein epitopes may be provided by one or more different NGAL antibodies.

Calibration with a particular device or technique may be conducted to determine a qualitative or quantitative amount of the formed complex which is representative of acute kidney injury. In a specific embodiment, wherein measurement is made by radioimmunoassay (RIA), an amount which is representative of acute kidney injury is 60 ng/ml or more NGAL protein. In another embodiment, wherein measurement is made by enzyme-linked immunosorbent assay (ELISA), an amount which is representative of acute kidney injury is 100 ng/ml or more NGAL protein.

In one embodiment, the methods employ a polyclonal NGAL antibody, for example as disclosed by Xu et al, *Journal of Immunological Methods*, 171:245-252 (1994), incorporated herein by reference. For example, as described by Xu et al, polyclonal antibodies against NGAL (HNL) are raised in rabbits by multiple site intracutaneous injections into the rabbits of a total of 72 μg of purified protein homogenized in Freund's complete and incomplete adjuvant. The specificity of the antibodies can be evaluated by double immunodiffusion (Devereux et al., *Nucleic Acid Research*, 12(1):387-394 (1984)) in agarose and tested against extracts of neutrophil granules and the following purified proteins: cathepsin G, elastase, myeloperoxidase, lysozyme, lactoferrin, eosinophil cationic protein (ECP) and eosinophil protein X (EPX/EDN). Other NGAL antibodies may, of course, be employed.

In one embodiment, the methods according to the invention comprise (a) contacting a body fluid sample from the individual with a polyclonal NGAL antibody, and (b) determining an amount of complex formed between NGAL from the sample and the polyclonal NGAL antibody using a detectable label, wherein the amount of the complex represents a level of acute kidney injury. In a specific embodiment, for example, the NGAL antibody comprises a polyclonal antibody and the amount of complex formed between NGAL protein in the sample and NGAL antibody is determined by conventional radioimmunoassay techniques. Such techniques are well known in the art and include the use of double radioimmunoassay techniques as well, wherein two polyclonal antibodies may be employed or wherein one polyclonal antibody and one monoclonal antibody may be employed. In another embodiment, the amount of complex formed between NGAL protein in the sample and NGAL antibody is determined by enzyme-linked immunosorbent assay (ELISA), wherein the ELISA employs at least one polyclonal NGAL antibody. ELISA techniques are also well known in the art. In specific embodiments using an ELISA procedure, the assay device includes a polyclonal NGAL antibody and a monoclonal NGAL antibody, one of which NGAL antibodies is bound to a substrate and the other of which NGAL antibodies is bound to the detectable label. In a more specific embodiment, the polyclonal NGAL antibody is bound to, i.e., immobilized on, the substrate. In a further embodiment, the polyclonal NGAL antibody is bound to a substrate and a monoclonal NGAL antibody is bound to the detectable label. Alternatively, the ELISA may employ an assay device including two different polyclonal NGAL antibodies, one of which NGAL antibodies is bound to a substrate and the other of which NGAL antibodies is bound to the detectable label. Other assay techniques known in the art may be employed wherein, for example, at least one polyclonal NGAL antibody is immobilized on a substrate and, in a more specific embodiment, the detectable label is bound to another NGAL antibody, which may be either a monoclonal NGAL antibody or a second polyclonal NGAL antibody.

Accordingly, the invention is also directed to devices and kits for such methods. In one embodiment, the assay device according to the invention comprises a polyclonal NGAL antibody immobilized on a substrate and adapted for contact with a body fluid sample, and a detectable label adapted to bind to a complex of NGAL protein and the immobilized polyclonal NGAL antibody. The detectable label may, in specific embodiments, be complexed with an NGAL antibody, either monoclonal or polyclonal, for binding to NGAL protein which complexes with the immobilized polyclonal NGAL antibody. The assay device may be provided as a "point of care" device or kit, facilitating use by medical personnel.

As will be apparent, the invention may be further used to monitor treatment of acute kidney injury, by analysis of multiple samples from an individual before and after or during a treatment regime. Such methods generally comprise contacting a first body fluid sample from the individual with a first assay device as described and determining an amount of complex formed between NGAL protein from the first sample and NGAL antibody in the first assay device, contacting a second body fluid sample from the individual, obtained after commencing the treatment, with a second assay device as described and determining an amount of a second complex formed between NGAL from the second sample and the NGAL antibody in the second assay device, and comparing the amount of the first complex with the amount of the second complex. A decrease in the amount of the second complex as compared with the amount of the first complex indicates the treatment is effective.

In another embodiment, the invention is directed to methods for determining an origin of neutrophil gelatinase-associated lipocalin (NGAL) protein in a sample from an individual. Such methods are particularly effective for distinguishing between kidney NGAL protein and neutrophil NGAL protein. In one embodiment, the methods comprise (a) determining relative amounts of monomeric, dimeric and heterodimeric forms of NGAL protein in the sample, and (b) comparing the determined amounts, wherein a predominate amount of monomeric and/or heterodimeric NGAL protein as compared with dimeric NGAL protein indicates NGAL protein originating from the individual's kidney, while an equal or predominate amount of dimeric NGAL protein as compared with monomeric or heterodimeric NGAL protein indicates NGAL protein originating in the individual's neutrophils. It has been discovered that kidney originating NGAL protein is substantially free of the dimeric form of NGAL protein, for example as shown by Western blotting. In a specific embodiment, the sample comprises urine. In another specific embodiment, the respective amounts of NGAL protein in the sample are determined by contacting the sample with an assay device including a monoclonal NGAL antibody. In another embodiment, the respective amounts of NGAL protein in the sample are determined by contacting the sample with an assay device including a polyclonal NGAL antibody. Any of the assay devices and techniques as described above, Western blotting, or other conventional techniques and/or devices may be employed.

As is demonstrated in Example 2 below, polyclonal and monoclonal antibodies identify (i.e., complex with) the monomeric, dimeric and heterodimeric NGAL protein forms. However, in the NGAL originating from kidney, the results are substantially free of the dimeric form of NGAL protein while the dimeric form of NGAL is predominate in the results from NGAL protein from neutrophils. While not wishing to be bound by theory, it is believed that the different NGAL's expose different epitopes, which are then picked up differently by, for example, the monoclonal antibodies. Thus, the comparison as described can differentiate kidney origin NGAL protein from neutrophil origin NGAL protein.

Various aspects of the invention are illustrated in the following Examples.

Example 1

This Example describes a study of NGAL determinations using NGAL antibody having binding capacity with more than two NGAL protein epitopes and comparisons with NGAL determinations using only two monoclonal antibodies.

Patients and Samples

A total of 59 adult patients undergoing cardiac surgery at the Uppsala University Hospital were included in the study. The age of patients ranged from 27-85, with a mean of 63, and the patients comprised 42 males and 17 females. The cardiac surgeries comprised 23 coronary artery bypass grafting, 15 aortic valve replacement, 4 mitral repair, 3 combined procedures, 8 left ventricle assist device implantations, and 6 other procedures.

Urine and blood samples were collected before operation and at various time points (2, 24, 48 and 72 hours) following cardiac surgery. The urine samples were immediately centrifuged at 3,000 rpm at 4° C. for 15 min. EDTA-plasma was obtained by centrifugation of the blood at 3,000 rpm at 4° C. for 15 min. All sample supernatants were immediately stored in aliquots at −20° C. Additionally, another 101 urine samples were collected from healthy employees and students and served as normal controls.

Assays of Urine Levels of NGAL

The levels of NGAL were measured by three different assays. A first assay technique employed a polyclonal-based RIA generally according to the teachings of Xu et al, supra. A second assay technique employed a polyclonal-monoclonal-based ELISA. The third assay technique employed a monoclonal-monoclonal-based assay. Thus, the first two techniques are according to the invention while the third technique was employed for comparison purposes.

More specifically, the polyclonal antibody based radioimmunoassay (RIA) was performed as previously described by Xu et al with some modifications. A 50 µL solution of either sample or standard (2 µg/L to 128 µg/L) were sequentially mixed with 50 µL of $I^{125}$-labelled NGAL and 50 µL of specific antibodies, diluted properly in the RIA assay buffer. The mixture was incubated at room temperature for 3 hours. Thereafter, 500 µL of solid phase second antibody coated cellulose suspension (AA-SAC1, IDS LTD, England) was added and incubated for 1 hour at 4° C. NGAL antibody complexes bound on anti-rabbit IgG antibody coated cellulose were separated and pelleted by means of centrifugation at 3400 rpm for 15 minutes. After decantation, the radioactivity was measured. The intra- and inter-assay coefficients of variation (CV) were less than 6% and 10%, respectively. The results of urine NGAL concentrations measured by the RIA assay device are designated NGAL RIA.

The polyclonal and monoclonal antibody-based ELISA device was developed in this study. Briefly, microtitre plates (Nunc Maxsorp, Agogent, Denmark) were coated overnight with anti-NGAL monoclonal antibody (100 μL/well, 1 μg/mL) diluted in Carbonate-Bicarbonate Buffer (0.05M $Na_2CO_3$—$NaHCO_3$, pH 9.6, Invitrogen Corporation, UK) at 4° C. Additional binding sites were blocked with Carbonate-Bicarbonate Buffer containing 2% bovine serum albumin (200 μL/well, Sigma-Aldrich, Steinhein, Germany) at 37° C. for 1 hour. 100 μL standards (0.1 ng/ml to 6.4 ng/ml) or diluted samples diluted in assay solution (PBS containing 0.2% bovine serum albumin, 0.1% Tween-20, 0.05% CTAB and 0.02% $NaN_3$) were added in duplicates and incubated at room temperature for 2 hours. Subsequently, 100 μL diluted rabbit anti-NGAL polyclonal antibody was added per well and incubated at room temperature for 1 hour, followed by 100 μL diluted horseradish peroxidase-conjugated antibodies (GE Healthcare, UK) and incubated at room temperature for another hour. The plates enzyme reaction was visualized with 3,3',5,5'-tetramethylbenzidine solution (100 μL/well, Sigma-Aldrich, Steinhein, Germany) at room temperature for 20 min, and stopped by addition of 100 μL/well 1M $H_2SO_4$. The plates were washed four times in a wash buffer (PBS containing 0.05% Tween-20) between all steps using Microplate Washer (Anthos fluido, Salzburg, Austria). Absorbance was measured at 450 nm with reference reading at 540 nm in blank wells by a microplate reader (SPECTRAmax 250, GMI, Inc., USA). The average intra-assay CV was 2.8% (range 0.5% to 4.7%) and the inter-assay CV was 6.3 (range 2.1 to 10.4%). The average recovery was 99% (range 93 to 105%). The results of urine NGAL concentrations measured by ELISA are designated NGAL ELISA.

The assay of NGAL on the double monoclonal assay was performed according to the instructions of the manufacturer. The intra- and inter-assay coefficients of variation (CV %) were less than 6%. The results of urine NGAL concentrations measured by this device are designated NGAL Mono-mono.

Urine creatinine levels were measured on the Architect instrument at the routine Department of Clinical Chemistry at the Uppsala University Hospital and served to correct the urine levels of NGAL for variations in urine dilutions. Thus, the urine levels of NGAL are presented as NGAL in μg/mmol creatinine. All measurements were made in duplicates and the laboratory investigators were blinded to the sample sources and clinical outcomes until the end of the study.

Western-Blotting of Urine NGAL

Western-blotting was performed as previously described by Towbin et al, *Proc. Natl. Acad. Sci. USA*, 76:4350-4 (1979). Briefly, 20 μL urine sample was applied to Nu-PAGE® 4-12% Bis-Tris Gel (Invitrogen Corporation, USA). After SDS-PAGE, the proteins were transferred onto a PVDF membrane by using Nu-PAGE® Transfer Buffer (Invitrogen Corporation, USA) at 25V for 1 hour. The additional binding sites of the PVDF membrane were blocked by a blocking solution (GE Healthcare, UK) for 1 hour. The blots were incubated with the mouse anti-NGAL monoclonal antibodies for 1 hour followed by 45 min incubation with peroxidase-conjugated secondary antibody (GE Healthcare, UK) Immunoblots were detected using enhanced chemiluminescence according to the instructions of the manufacturer (Amersham ECL™ Western Blotting System, GE Healthcare, UK).

Additional Assays

Plasma levels of creatinine and cystatin-C were measured using routine procedures at the Department of Clinical Chemistry, Uppsala University Hospital.

Statistical Analysis

Mann-Whitney's and Wilcoxon's non-parametric tests for unpaired and paired comparisons, linear regression analysis, one-way analysis of variance (ANOVA) were performed by Medcalc 9.5 (MedCalc Software, Mariakerke, Belgium) and STATISTICA 8.0 (StatSoft, Inc., Tulsa, USA). The statistical significance was set at $p<0.05$.

Results

Plasma creatinine levels before and up to 78 hours after operation are given in FIG. 1 and show no differences between the time periods. The clinical outcome indicated that three subjects had signs of acute kidney injury with postoperative plasma creatinine elevations of >50%.

Urine Levels of NGAL

Figure 2A:
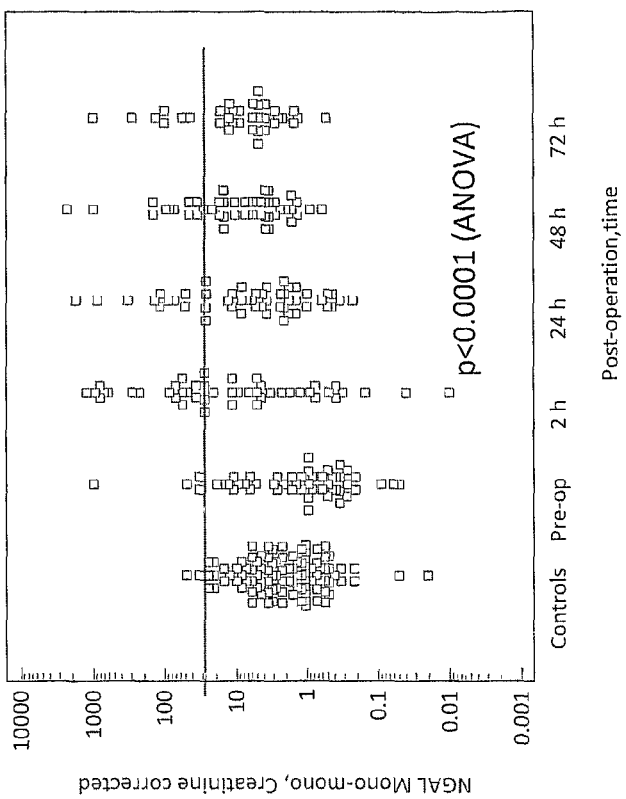
FIGS. 2A and 2B show pre- and post-operative levels of NGAL in urine measured using an RIA assay employing polyclonal antibody and an assay using two monoclonal antibodies, respectively, as described in Example 1. The levels of healthy subjects are also shown. The horizontal line indicates the upper 97.5, the percentile of the healthy controls. The overall differences between pre- and post-operative levels were estimated by ANOVA and shown on the figures. For both assays, the post-operative levels were significantly different from pre-operative levels at all three time points ($p<0.001$).
Figure 2B:
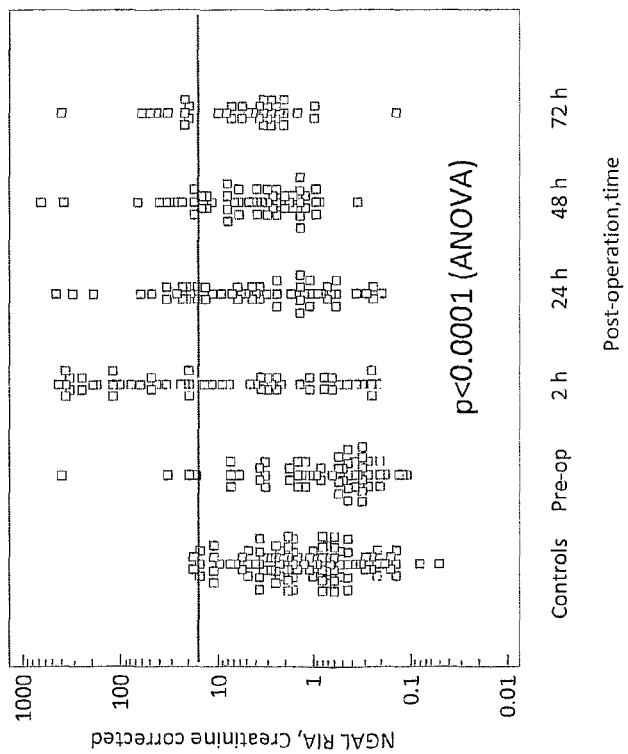

The levels of NGAL in urine obtained from healthy subjects and patients undergoing cardiac surgery were measured with using the three described techniques. The results determined using the RIA and Mono-mono techniques, respectively are shown in FIGS. 2A and 2B. The pre-operative levels were similar to normal controls. Two hours after operation, the levels increased significantly ($p<0.0001$) with about half the patients having levels above the upper limit of normals. The fold increases of medians were 18.7 when measured with the RIA and 15.6 and 11.4-fold increases when measured with the ELISA and the Mono-mono assays, respectively. After 24 hours, the levels were again reduced, but still higher than pre-operative levels. The levels stayed significantly higher during the whole postoperative period ($p<0.0001$). At 72 hours, the fold increases were respectively 6.8, 8.5 and 5.9 for the RIA, ELISA and Mono-mono assays. Similar patterns over time were seen with all three assays.

Relation to Extracorporeal Circulation Time (ECC)

Figure 3C:
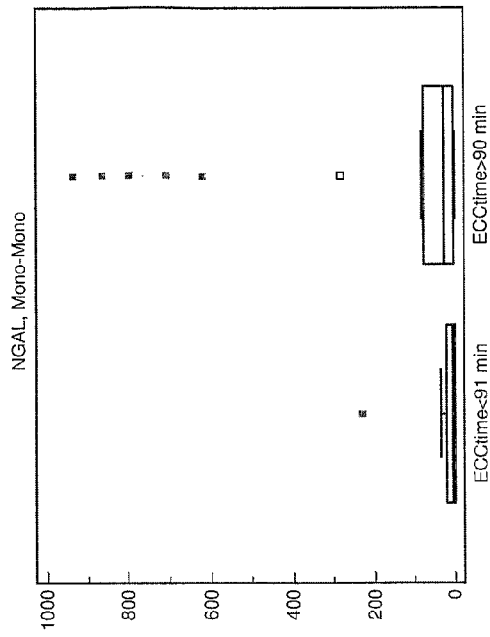
FIGS. 3A-3C show box-plots of the relationship between urine NGAL levels 2 hours post operation and the extracorporeal circulation time (ECC time) measured using an RIA assay employing polyclonal antibody, an ELISA assay using polyclonal and monoclonal antibodies, and an assay using two monoclonal antibodies, respectively, as described in Example 1. Statistical differences and fold increase of medians are indicated.
Figure 3A:
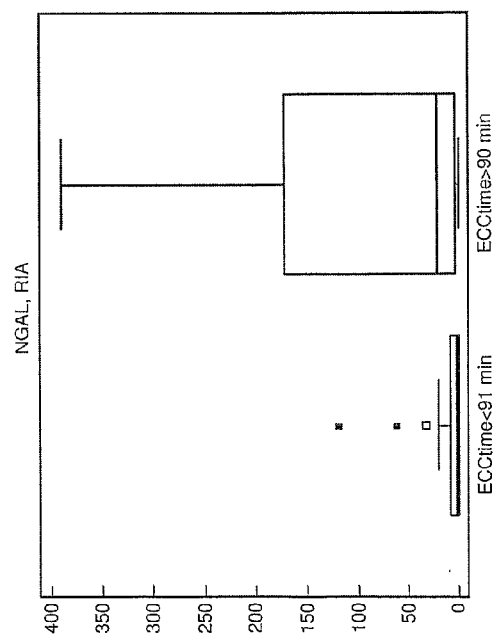
Figure 3B:
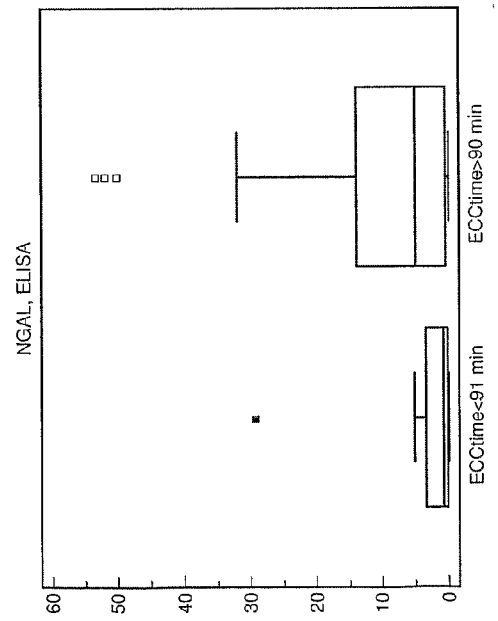

Significant positive correlations between ECC-time and the levels of NGAL obtained 2 hours postoperatively were found when measured in urine by the RIA technique ($r^2=0.30$, $p<0.0001$) and the ELISA technique ($r^2=0.16$, $p=0.006$). However, these correlations were not found with the Mono-mono technique. When subgrouped by ECC-time greater or less than 90 min, the RIA-results were increased 12.6-fold in the 2 hour postoperative samples ($p=0.006$). The ELISA-results were increased 6.5-fold ($p=0.027$) and the Mono-mono results 5.2-fold ($p=0.07$), as shown in FIGS. 3A-3C.

Relationship Between Urine Levels of NGAL and Kidney Function

Figure 4A:
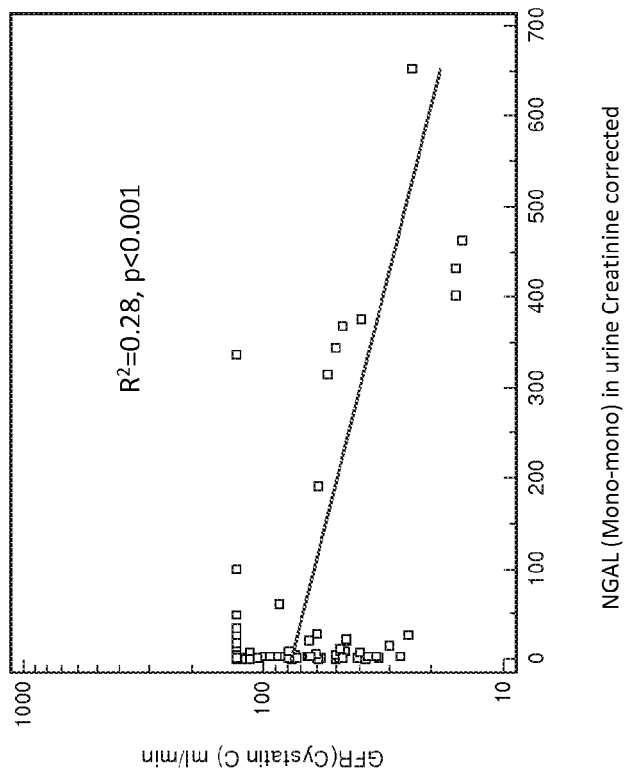
FIGS. 4A and 4B show the relationship between urine NGAL levels and GFR (plasma cystatin C) measured using an RIA assay employing polyclonal antibody and an assay using two monoclonal antibodies, respectively, as described in Example 1. The results of linear regression analysis are shown.
Figure 4B:
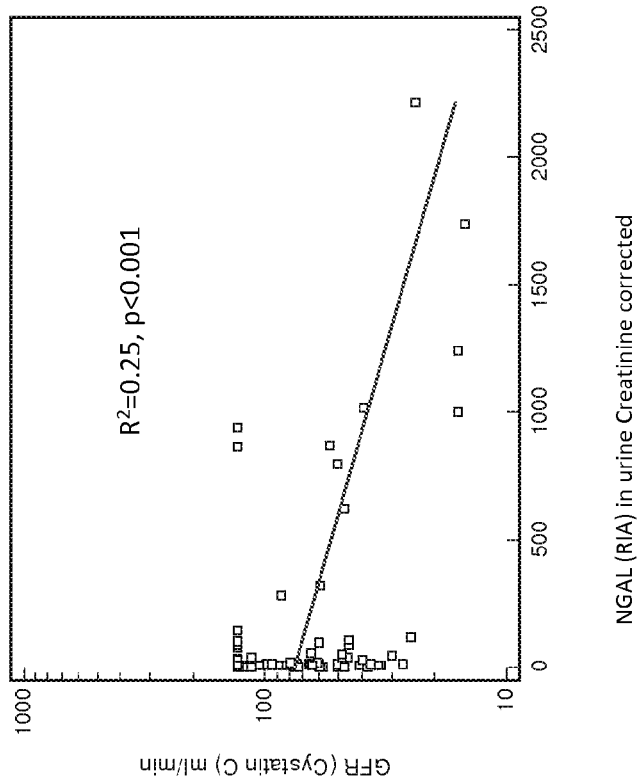

Plasma levels of creatinine and cystatin-C were measured as indicators of kidney function. As shown above, the creatinine levels stayed unaltered in most subjects with only three subjects having postoperative signs of acute kidney injury as defined by an increase of >50%. Cystatin-C levels were used to calculate glomerular filtration rate (GFR). In a univariate analysis, GFR was related to NGAL (RIA) ($r^2=0.28$, $p<0.001$) and NGAL (Mono-mono) ($r^2=0.25$, $p<0.001$) as shown in FIGS. 4A and 4B. The relationship between urine NGAL and plasma creatinine was also analyzed. The subjects were classified into two groups according to the percentage increase of plasma creatinine during the 72 hours postoperative period as compared with baseline (<120% or >119%). The 2 hours postoperative levels of NGAL (RIA) were significantly higher in the group in which creatinine levels rose >119% (p=0.03) in contrast to NGAL (Mono-mono) levels which were not significantly elevated (results not shown).

Correlations Between the Three NGAL Assays

Figure 5:
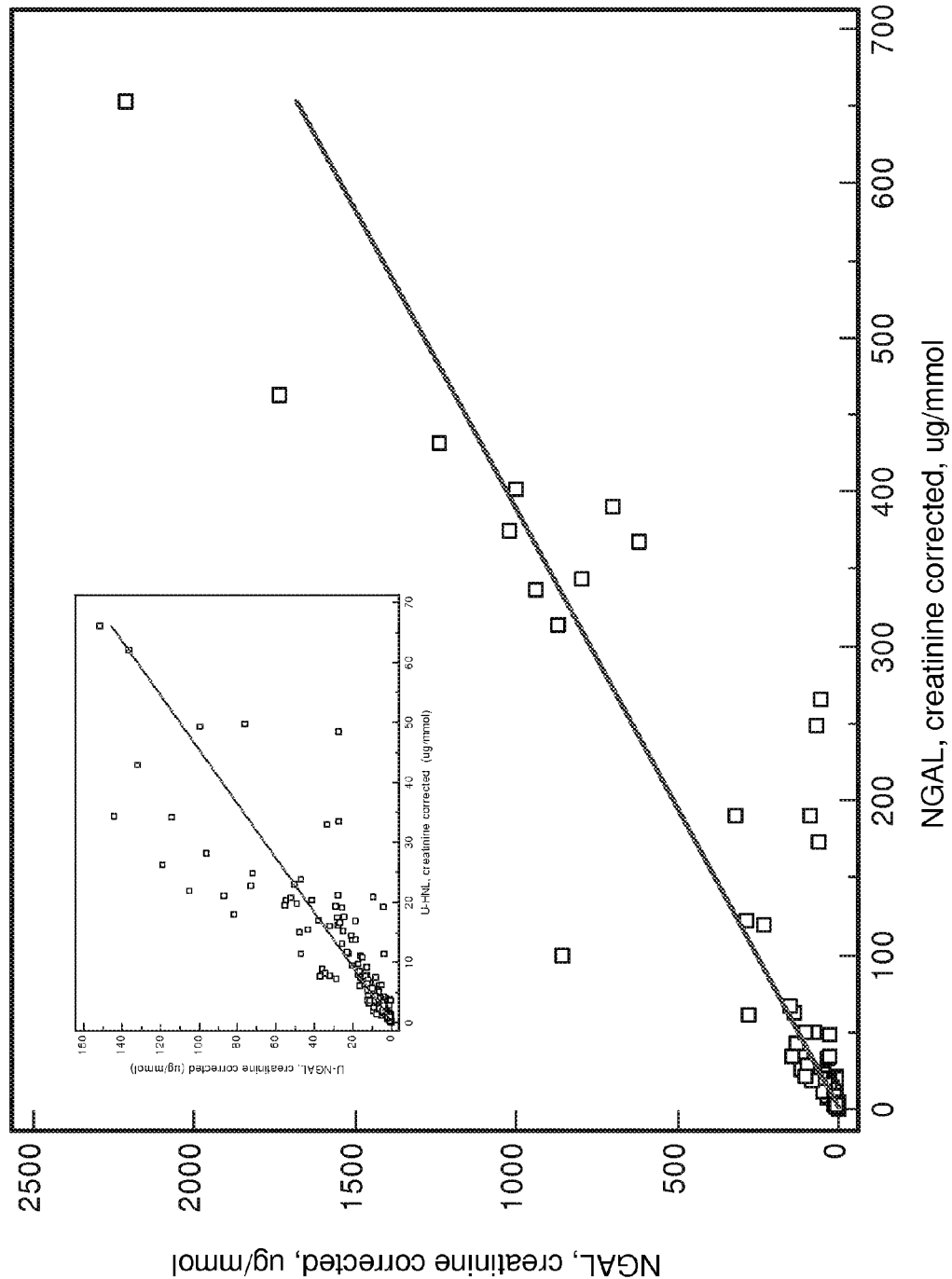
FIG. 5 shows the relationship between measurements of NGAL protein using RIA employing a polyclonal NGAL antibody and an assay using two monoclonal antibodies, in urine, as described in Example 1. Linear regression analysis: $r^2=0.86$, $p<0.0001$, $n=331$. The insert shows the relationship between the two assays at the lower end of the concentrations.

The overall correlation between NGAL (RIA) and NGAL (Mono-mono) is shown in FIG. 5 ($r^2$=0.86, p<0.0001, n=331). The correlations at different time points are given in Table 1 and show very good correlations with $r^2$'s ranging between 0.952-0.996, but with the exception of results obtained 2 hours postoperatively. At this time point the $r^2$ was 0.680 and significantly lower than the rest (p<0.0001). The relationship between NGAL (RIA) and NGAL (Mono-mono) in the cohort of seemingly healthy subjects was $r^2$=0.887 and also significantly different from the 2 hour results (p=0.001). A Passing-Bablok regression analysis of all 331 results showed the equation of HNL (RIA)=0.6553+0.5358×NGAL (Mono-mono) with a significant deviation from linearity (p<0.01), which was also the case for the comparison of the NGAL (Mono-mono) assay and the NGAL (ELISA) assay, NGAL (ELISA)=0.0370+0.1135×NGAL (Mono-mono). However, the comparison of the NGAL (RIA) and the NGAL (ELISA) assays gave the equation NGAL (ELISA)=–0.002192+0.2002×NGAL (RIA) with no deviation from linearity.

Molecular Forms of NGAL in Urine

The major forms of NGAL found in urine before and after cardiac surgery had apparent molecular weights of 25 (monomer), 45 (homodimer) and 90-130 kDa (complexes with MMP-9), respectively. The presence of these different forms varied before and after surgery. Ratios between the homodimers and the monomers based on Western-blot scanning were examined. It is shown that the relative presence of homodimers increased up to 24 hours postoperatively (p=0.02) after which the ratio has a tendency to decrease.

Discussion

The results presented herein show that the choice of antibodies in the NGAL assay is critical in order to identify the many different variants of NGAL excreted in the urine under various conditions. Particularly, assays employing NGAL antibody having the capacity to react with more than two NGAL protein epitopes provide improved sensitivity.

This study involved adult patients undergoing cardiac surgery. Acute kidney injury is one of the most serious postoperative complications that may affect these patients. In this study the average levels of plasma creatinine remained unaltered, with only three subjects having elevations of >50% as signs of acute kidney injury. In spite of this, 10-100-fold increases in NGAL levels in urine were found in about half the patients, only 2 hours after termination of the operation. Moreover, the NGAL levels stayed elevated for the whole observation period. Overall the urine levels of NGAL showed a weak, but significant relationship with kidney function as measured by plasma levels of cystatin C or creatinine, which supports the notion of NGAL being an earlier and more sensitive marker of kidney dysfunction. Indeed two of the three patients with creatinine elevations >50% had highly increased NGAL levels 2 hours after operation. It is apparent from this study that the major increase in NGAL occurred early after operation in half of the patients, but that this increase was only temporal and then followed by a gradual increase the following days which involved all patients. Thus, while not wishing to be limited by theory. these patterns may reflect different mechanisms involved in urine excretion of NGAL in urine. The early phase may reflect the excretion of preformed NGAL from different sources such as kidney epithelium and accumulating neutrophils, whereas the delayed excretion may reflect de novo synthesis in the kidney. Findings of variations in the extent to which the many different molecular sizes of NGAL occur in urine at different times also suggest that different mechanisms are involved.

The comparison of the three different assays showed significant differences. Overall, the assays were highly correlated, but with some obvious exceptions. These exceptions turned out to be concentrated in the samples obtained 2 hours post operation, as a suggestion of the fact that the three assays under these circumstances partly measure different molecular variants of NGAL. These differences were further exemplified by the fact that the results of the RIA and ELISA assay employing polyclonal antibodies showed closer relationships to clinical variables such as length of extracorporeal circulation time and kidney function than the Mono-mono assay. These results therefore show that the identification of all forms of NGAL in urine is important for the clinical performance of the assay. The RIA is a polyclonal-based assay, which likely addresses all available epitopes in the molecule, whereas the monoclonal-monoclonal-based assay addresses only selected epitopes, some of which may or may not be disguised by complex formations and other molecular alterations. The polyclonal-monoclonal-based ELISA assay had characteristics somewhat in between these two extremes, which may be explained by the fact that this configuration allows the recognition of more epitopes than a double monoclonal assay but somewhat less than a purely polyclonal-based assay. In summary, the described results confirm that NGAL is a useful early biomarker of postoperative kidney injury when measured in urine and newly demonstrate that the antibody configuration of the assay has an impact on the clinical performance of the assay, since some forms of NGAL may not be identified by assays with restricted antibody specificities.

Example 2

This Example describes a study of NGAL determinations with respect to monomeric, dimeric and heterodimeric forms in determining the NGAL protein origin.

Urine Samples and Separation on Gel Filtration

In total, 33 urine samples were collected pre-operation and at 2 h and 24 h time points following cardiac surgery. The urine samples were immediately centrifuged at 3,000 rpm for 15 min at 4° C. and stored in aliquots at –20° C. Gel filtration of one urine sample at 2 h post operation was performed on a Superdex™ 75 HR 10/30 prepacked column using the FPLC-system (Amersham Pharmacia Biotech AB, Uppsala, Sweden). Fractions of 250 L were collected and stored at –20° C. The elution buffer was PBS. NGAL in the fractions was determined using the RIA and ELISAs described below.

Sensitive ELISAs for NGAL Quantification

Six ELISAs based on different antibodies for NGAL quantification were employed, namely 1) Mab697-polyclonal (the monoclonal-polyclonal ELISA as described in Example 1), 2) Mab764-Mab765, 3) Mab764-polyclonal, 4) polyclonal-Mab765, 5) polyclonal-polyclonal, and Mab697-Mab765. The basic protocols for these five ELISAs are the same as described in Example 1 except for the specific antibodies used in the assay. Briefly, the 96-well microtitre plates (Nunc Maxsorp, Agogent, Danmark) were coated with rabbit polyclonal or mouse monoclonal antibodies (Mab697 and Mab764) against human NGAL %. (Diagnostics Development, Uppsala, Sweden). Samples and standards (ranging from 0.039-5 μg/L) (100 μL/well) were incubated for 60 min (urine samples and gel filtration fractions) or 90 min (cell culture supernatants) at room temperature (RT). Subsequently, 100 μL/well of diluted biotinylated rabbit polyclonal antibodies or mouse monoclonal antibody (Mab765) against human NGAL were added and incubated at RT for 60 min, followed by the addition of 100 μL/well of diluted streptavidin conjugated horseradish peroxidase (GE Healthcare, United Kingdom) (30 min at RT). The plates were washed four times in a washing buffer (PBS containing 0.05% Tween-20) using a Microplate Washer (Anthos fluido, Salzburg, Austria) between all steps. The enzyme reaction was visualized by 3,3',5,5'-tetramethylbenzidine solution (100 μL/well) (Sigma-Aldrich, Steinhein, Germany) as substrate at RT for 15 min and the reaction was stopped by adding 1 M $H_2SO_4$ (100 μL/well). Absorbance was read at 450 nm with a spectrophotometer (SPECTRAmax 250, GMI, Inc., USA).

Polyclonal Antibody Based RIA for NGAL Quantification

The RIA was performed as described above. Briefly, a 50 μL of either sample or standards (2 μg/L-128 μg/L) was mixed with 50 μL of $I^{125}$-labelled NGAL and 50 μL of specific antibodies. The mixture was incubated for 3 h at room temperature. Thereafter, 500 μL of solid phase second antibody coated cellulose suspension (AA-SAC1, IDSLTD, United Kingdom) was added and incubated for 1 h at 4° C. NGAL-antibody complexes bound on anti-rabbit IgG antibody coated cellulose were pelleted by centrifugation. After decantation, the radioactivity was measured.

HK-2 Culture and the Expression of NGAL Protein

HK-2 (human kidney 2, CRL-2190) was purchased from the American Type Culture Collection (ATCC). It is a human renal proximal tubular epithelial cell line derived from normal kidney. The cells were immortalized by transduction with human papilloma virus 16 (HPV-16) E6/E7 genes. The cells were cultured either in complete growth medium (Keratinocyte Serum Free Medium (K-SFM) supplemented with 0.05 mg/ml bovine pituitary extract (BPE) and 5 ng/ml human recombinant epidermal growth factor (EGF) (Invitrogen-Gibco®, United Kingdom)) or in incomplete growth medium at 37° C. in a humid atmosphere with 5% $CO_2$. Additionally, the cells were cultured with specific stimuli including cytokines (IL-1β or TNF-α) (Sigma-Aldrich, Steinhein, Germany) and LPS (Invitrogen-Giboco®, United Kingdom). $0.5 \times 10^5$ cells and 1 ml complete growth medium per well were seeded in 24-well plates (FALCON®, USA). Following 48 h subculture, the complete growth medium was removed and the monolayer (about 90% confluence) was washed twice with PBS (Invitrogen-Giboco®, United Kingdom). The cells were cultured with conditioned media for a 72 h period. The media supernatants were harvested for NGAL quantification at 2 h, 12 h, 24 h, 48 h and 72 h, respectively.

Assessment of NGAL Gene Expression by RT-PCR

The normal cultured and 1 ng/mL IL-1β induced HK-2 cells were harvested at 2 h, 4 h, 6 h, 8 h, 12 h and 24 h for total RNA isolation. RNA was extracted using RNeasy® Mini Kit (QIAGEN, United Kingdom) according to the manufacturer's protocol. The first-strand cDNA was synthesized using SuperScript III reverse transcriptase (Invitrogen, United Kingdom) with 200 ng total RNA. Polymerase chain reaction (PCR) was carried out by using Taq DNA polymerase (Invitrogen, United Kingdom) in the DNA Engine PCR machine (PTC-200) (Bio-Rad, USA). The sequences of the specific oligonucleotide primers for NGAL (5'-TCACCTCCGTCCTGTTTAGC-3' and 5'-CGAAGTCAGCTCCTTGGTTC-3') and β-actin (5'-TTCTACAATGAGCTGCGTGTGG-3' and 5'-GTGTTGAAGGTCTCAAACATGAT-3') were selected according to the literature and synthesized by Thermo SCIENTIFIC (Germany). The initial denaturation condition is 94° C. for 2 min PCR amplification was performed using a 30 sec denaturation step at 94° C., followed by a 30 sec annealing step at 60° C. (for NGAL) or 59° C. (for β-actin), and a 30 sec extension at 72° C. A total of 30 cycles were carried out for both genes followed by a final extension for 10 min at 72° C. PCR products were separated by 2% agarose gel electrophoresis, and were detected by ethidium bromide staining. Expected size of PCR produces (242 bp and 119 bp for NGAL and β-actin, respectively) was verified by reference to a 50-bp DNA ladder (DirectLoad™ DNA Marker) (Sigma-Aldrich, Steinhein, Germany).

Western Blotting

The neutrophil granule release products were obtained as described. HK-2 conditioned media supernatants at the 72-h time point were harvested, and supplemented with 0.1 mM PMSF (Sigma-Aldrich, Steinhein, Germany) and Complete™ protease inhibitor cocktail tablets (Roche, Mannheim, Germany). The supernatants were concentrated using Amicon® Ultra-4 centrifugal filter devices (10,000 MW) (Millipore, USA). SDS-PAGE and Western blotting were performed according to the manufacturer's instructions. Briefly, 25 μL of either urine or concentrated conditioned supernatants or neutrophil release products were applied to Nu-PAGE® 4-12% Bis-Tris Gel (Invitrogen, USA) under non-reducing conditions. The proteins were transferred onto a Hybone-P PVDF membrane (GE Healthcare, United Kingdom) by using Nu-PAGE® Transfer Buffer (Invitrogen, USA) at 25V for 1 hour. The additional binding sites of the PVDF membrane were blocked by a blocking solution (GE Healthcare, United Kingdom) for 1 h. The blots were incubated overnight at RT with either rabbit polyclonal antibodies or mouse monoclonal antibodies (Mab 697, Mab 699, Mab 763, Mab 764, or Mab 765) or a mixture of monoclonal antibodies against human NGAL followed by 1 h incubation with peroxidase-conjugated secondary antibodies (GE Healthcare, United Kingdom) Immunoblots were detected using enhanced chemiluminescence according to the instructions of the manufacturer (Amersham ECL™ Western Blotting System, GE Healthcare, United Kingdom).

Statistical Analysis

Student's t-test and one-way analysis of variance (ANOVA) were performed by STATISTICA 8.0 (StatSoft, Inc., Tulsa, USA) and Medcalc 9.5 (MedCalc Software, Mariakerke, Belgium). Values are presented as means±SD and medians with interquartile ranges. $p<0.05$ were considered as significant.

Results

Detection of NGAL Molecular Forms in Urine by Western Blotting

Figure 6:
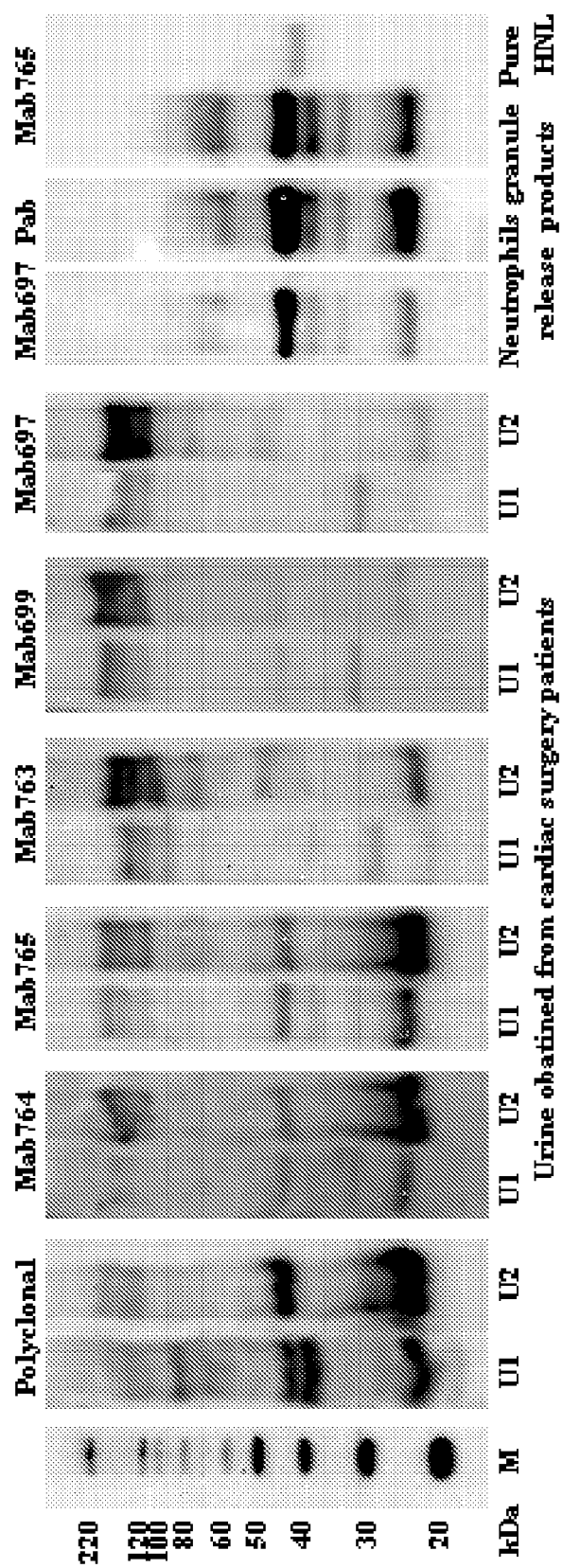
FIG. 6 shows Western blotting results as described in Example 2 of different molecular forms of NGAL in urine samples U1 and U2 obtained from two patients undergoing cardiac surgery.

One rabbit polyclonal and five mouse monoclonal antibodies against NGAL were used to identify the molecular forms of NGAL present in urines obtained from cardiac surgery patient. The five monoclonal antibodies were shown by Biacore experiments to react to different epitopes. As shown in FIG. 6 with two representative urine samples (U1 and U2), notable differences between the antibodies' performances were found. Three major bands were regularly identified by the polyclonal antibodies and were identified as the monomeric and dimeric forms of NGAL and the complexed, heterodimeric forms of NGAL. These three forms were also detected by Mabs764 and 765. However, additional bands were also seen with either antibody. The polyclonal antibody, however, seemed to have a stronger affinity to the dimer and a weaker affinity to the heterodimer than the two monoclonals. The Mabs764 and 765 had very similar performances on detecting all three molecular forms. The affinities of Mab764 and Mab765 to NGAL from high to low were monomeric, heterodimeric and dimeric forms, respectively. It is also shown that Mabs763, 699 and 697 have strong affinities to heterodimeric forms, whereas the affinities to the dimeric and monomeric forms were weak. However, the ability of the polyclonal antibodies and the Mabs765 and 697 in detecting monomeric and dimeric forms in supernatants of stimulated neutrophil granulocytes seemed very similar.

Performances of the RIA and Five ELISAs for Measuring NGAL in Urine

The performance characteristics of the RIA and the five ELISAs are shown in Table 1:

Measurements of NGAL by Different Assays Following Gel Filtration of Urine

Figure 7:
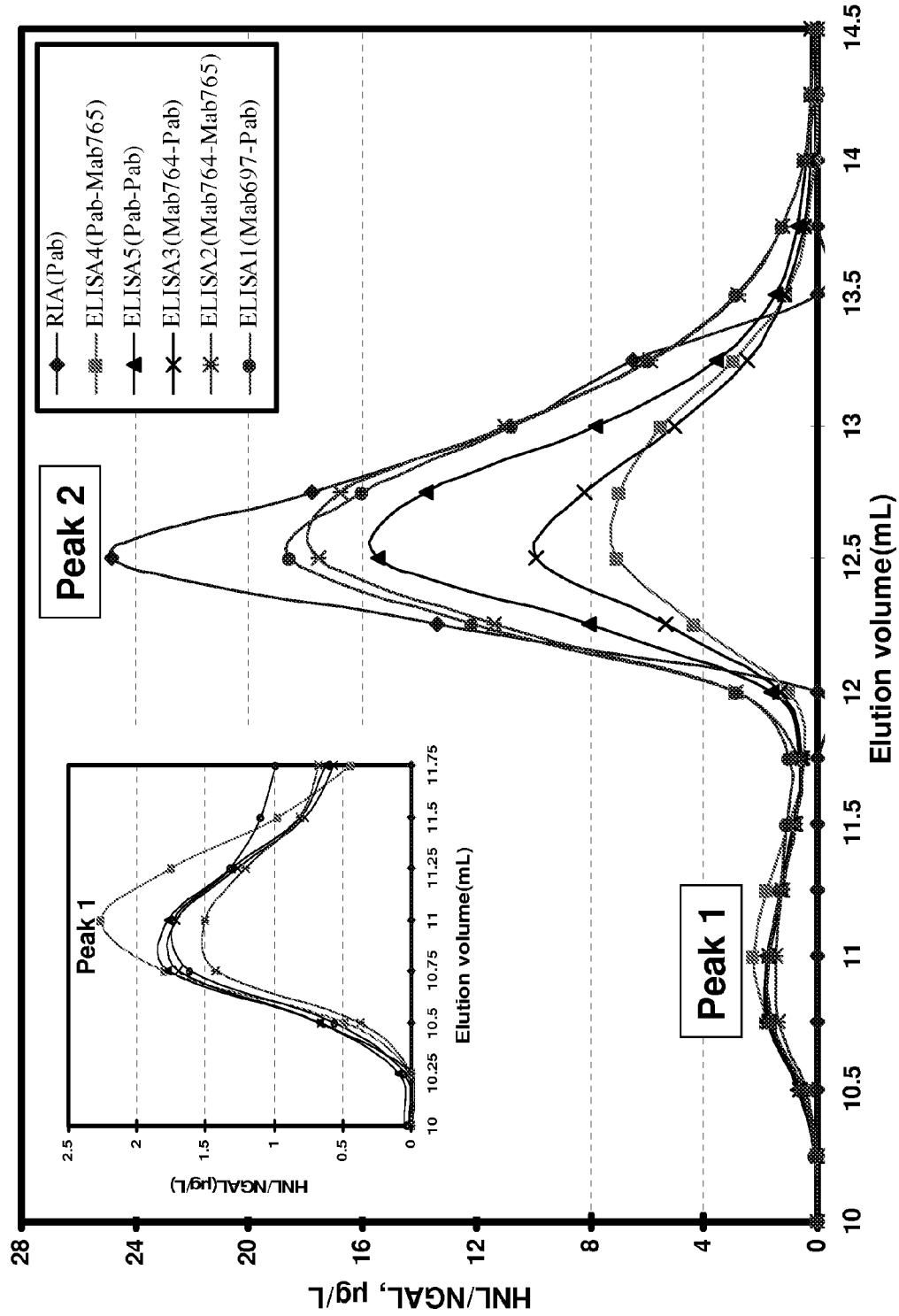
FIG. 7 shows measurements of NGAL in the fractions from Superdex™-75 gel filtration of urine using different antibody based assays as described in Example 2. The major molecular forms of NGAL in the peak 1 and the peak 2 are dimer and monomer, respectively. The insert is the amplification of peak 1.

Based on the Western blotting results, the following two sets of experiments were undertaken to investigate the performances of the assays in the detection of different forms of NGAL. Gel filtration of one urine sample at 2 h post operation was performed on a Superdex™ 75 HR column NGAL levels in the fractions were measured by RIA and the five ELISAs and shown in FIG. 7. Two peaks corresponding to elution volumes of the monomeric and dimeric forms, respectively, were obtained by the five ELISAs, but only one peak with the RIA. The latter was probably due to insufficient sensitivity of the RIA. The highest levels of NGAL in peak 2 were obtained with the RIA and the lowest levels with ELISA 1 (Mab697-Polyclonal based ELISA). All ELISA assays but ELISA 1 measured similar levels in peak 1, i.e. dimeric NGAL (FIG. 2 insert). ELISA 1 measured higher levels of the dimeric NGAL.

TABLE 1

Measurements of HNL/NGAL in urine samples collected from patients undergoing cardiac surgery by different assays

| Assay | Pre-op µg/L | 2 h post-op µg/L | 24 h post-op | Fold increase (Pre-op/ 2 h post-op) | Student's t-test p-value | ANOVA p-value |
|---|---|---|---|---|---|---|
| RIA | 7.19 (2.9-20.3) | 248.20 (109-316.1) | 26.96 (16.3-50.71) | 34.5 | 0.000011 | 0.0000020 |
| ELISA 1 (Mab697-Polyclonal) | 0.94 (0.15-3.13) | 28.82 (23.32-37.96) | 4.75 (2.59-9.89) | 30.7 | 0.00035 | 0.00027 |
| ELISA 2 (Mab764-Mab765) | 6.22 (1.16-12.8) | 192.80 (78.2-287) | 15.50 (9.55-40.7) | 31.0 | 0.000055 | 0.00002 |
| ELISA 3 (Mab764-Polyclonal) | 3.08 (1.08-10.81) | 239.10 (61.6-296.40) | 19.80 (6.25-55.35) | 77.6 | 0.000053 | 0.00015 |
| ELISA 4 (Polyclonal-Mab765) | 2.26 (0.79-7.84) | 164.10 (45.9-207.1) | 13.05 (5.89-40.2) | 72.6 | 0.00010 | 0.000094 |
| ELISA 5 (Polyclonal-polyclonal) | 2.96 (1.13-12.68) | 220.00 (58.4-249.9) | 19.00 (7.5-58.15) | 74.3 | 0.000024 | 0.000079 |
| ELISA 6 (Mab697-Mab765) | 1.27 (0.32-3.46) | 30.00 (6.4-30) | 3.46 (2.07-10.35) | 23.6 | 0.00099 | 0.00012 |

Values are presented as medians and interquartile range. The students's t-test was performed between preoperative and 2 h postoperative groups, and the ANOVA was performed among preoperative and 2 h and 24 h postoperative groups.

The levels of NGAL in urine obtained pre-operation and at 2 h and 24 h post operation were measured and the median levels of NGAL obtained by the assays are shown in Table 1. The median levels of NGAL pre-operation and 2 h post operation measured by RIA were the highest among the seven assays. On the other hand, the levels obtained by Mab697-based ELISA (ELISA 1 and ELISA 6) were significantly lower than the other assays. Table 1 shows the differences in levels pre- and 2 h post operation as well as overall differences during the 24 hour period. Highly significant differences pre- and postoperatively were seen with all assays. Fold increases of median levels preop vs 2 h postop were highest and >70 when measured by ELISA 3 (Mab764-Polyclonal), ELISA 5 (polyclonal-polyclonal) or ELISA 4 (polyclonal-Mab765), and 23-34-fold when measured by RIA, ELISA 2 (Mab764-Mab765), ELISA 1 (Mab 697-polyclonal) or ELISA 6 (Mab697-Mab765).

NGAL is Up-Regulated in HK-2 Cells when Grown Under Stressful Conditions

HK-2 cells were cultured at different lengths of time with Keratinocyte Serum Free Medium (K-SFM), K-SFM either supplemented with 0.05 mg/mL bovine pituitary extract (BPE) or 5 ng/mL human recombinant epidermal growth factor (EGF), or ATCC recommended complete growth medium (K-SFM supplemented with 0.05 mg/mL BPE and 5 ng/mL EGF) followed by culture for 48 h under standard conditions. The levels of NGAL in the culture supernatants were determined at different time points (2 h, 12 h, 24 h, 48 h and 72 h) over a 72 h period by ELISA 4. After 12 h to 72 h in culture, the levels of NGAL in K-SFM culture supernatants were higher than in the other three culture media (FIG. 8). The lowest levels were found in cells grown in complete growth medium. The results also suggest higher levels of NGAL in supernatants of cells grown in K-SFM supplemented with BPE as compared to cells grown in K-SFM supplemented with rEGF. Overall, these results show up-regulation of NGAL production under stressful conditions in which the cells were deprived of necessary growth factors.

NGAL is Up-Regulated in HK-2 Cells by IL-β, LPS and TNF-α

Figure 9A:
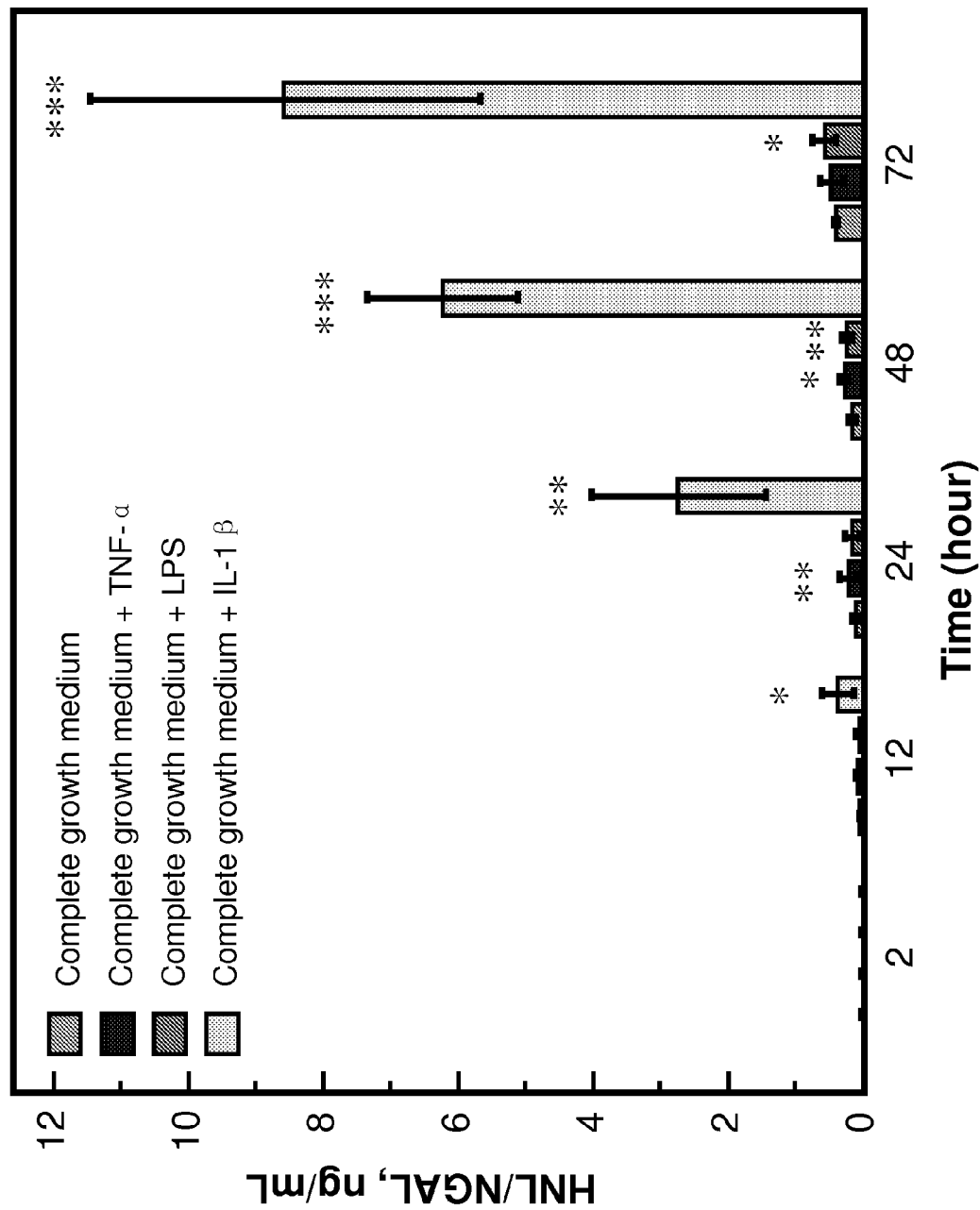
FIGS. 9A and 9B show levels of NGAL secreted from HK-2 cells grown in either complete medium or complete medium supplemented with stimuli (FIG. 9A), or grown in Keratinocyte Serum Free Medium (K-SFM) or K-SFM supplemented with stimuli (FIG. 9B). Values are means±SD from duplicate assays of three independent experiments. The markers *,  and * represent $p<0.05$, $p<0.01$ and $p<0.001$, respectively.
Figure 9B:
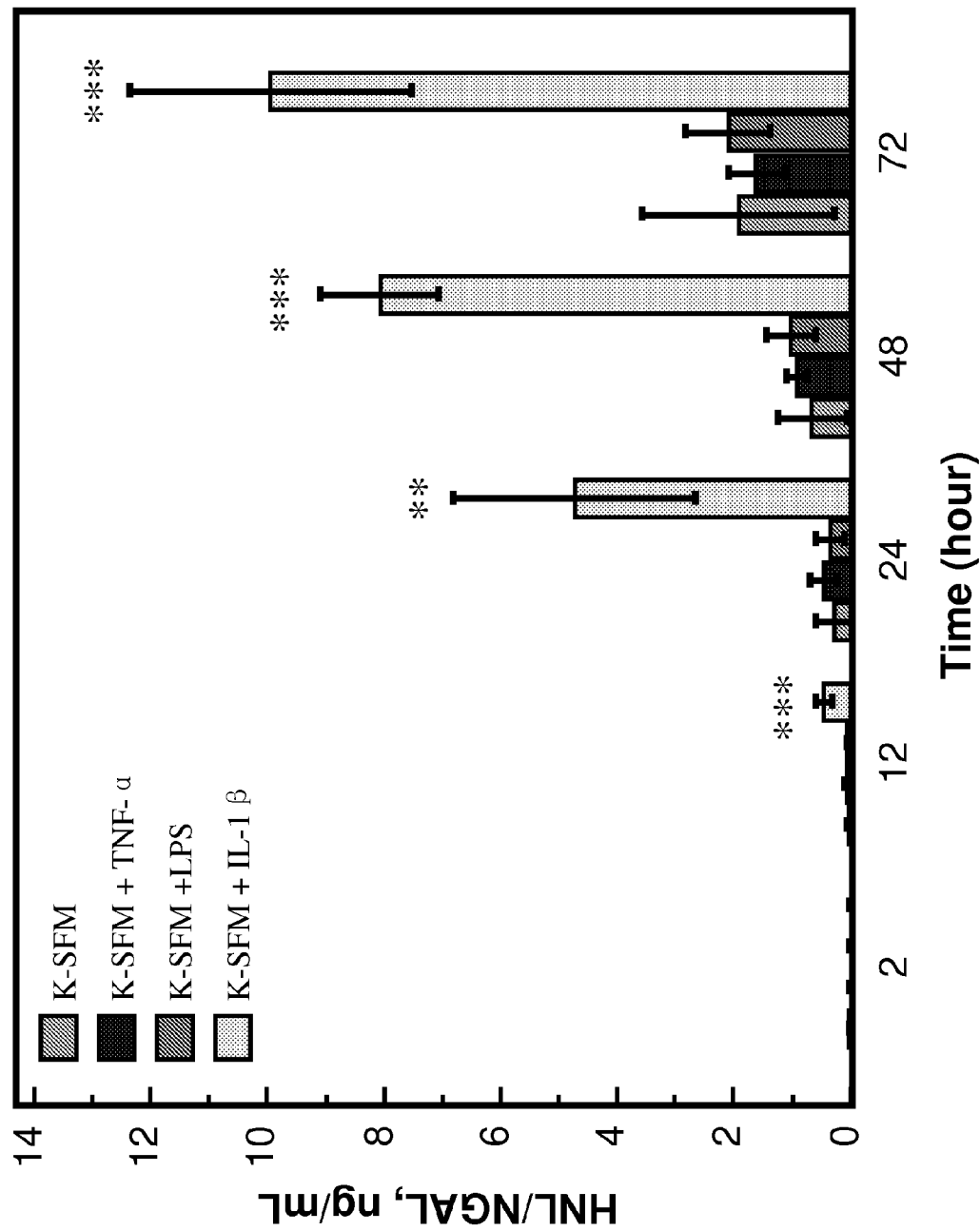

HK-2 cells were grown with complete growth medium for 48 h after which the cells were further grown for various lengths of time in the presence of complete growth medium supplemented with either IL-β (1 ng/mL, human), LPS (125 ng/mL, *Klebsiella pneumonia*) or TNF-α (20 ng/mL, human). As is shown in FIG. 9A, IL-β induced highly significant elevations of NGAL levels in the supernatant (8.9- to 41.9-fold increase). Also the incubation with TNF-α and LPS induced some elevations of NGAL in the supernatants (2.2 and 1.6-fold, respectively), but significantly less than IL-β (p<0.001). HK-2 cells were also cultured with K-SFM supplemented with IL-β, TNF-α or LPS. Significant elevations of NGAL were seen with IL-β (1.3- to 12.8-fold increase), but not with TNF-α or LPS (FIG. 9B). Compared to cells grown in complete growth medium these elevation were, however, significantly less (p<0.001).

Molecular Forms of NGAL Produced by HK-2 Cells

Figure 10:
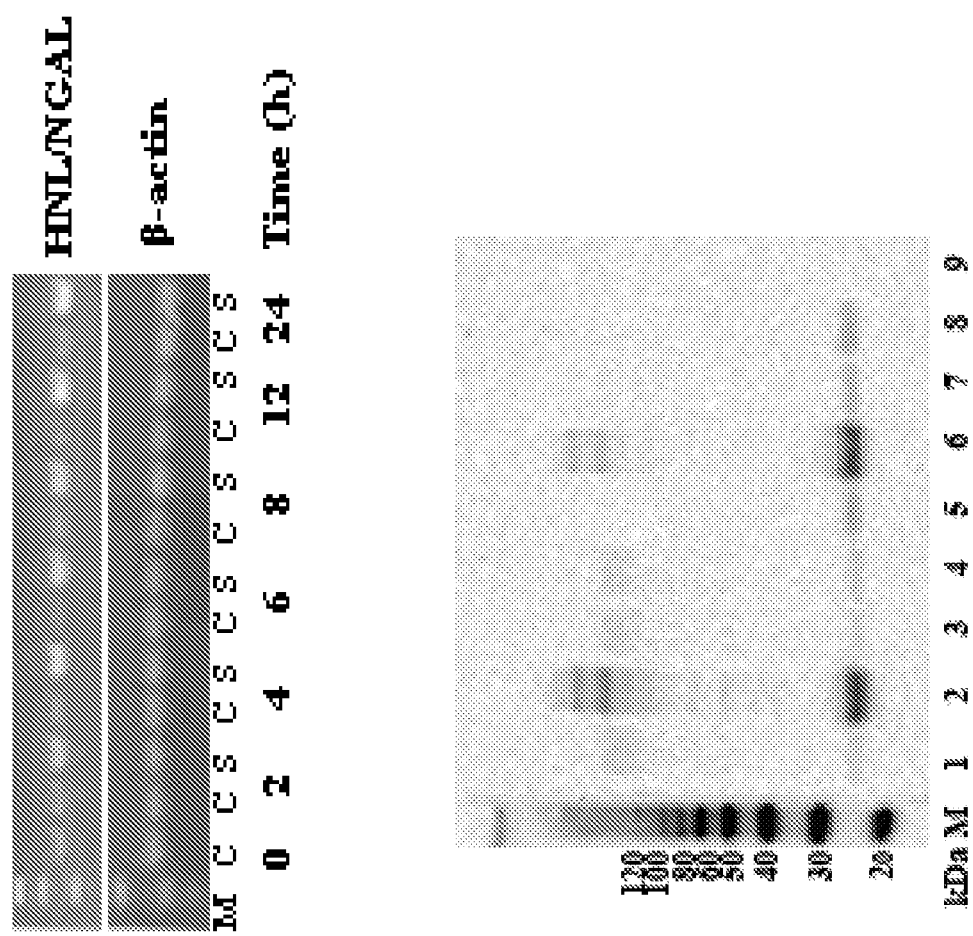
FIG. 10 shows in the lower panel detection of NGAL secreted from HK-2 cells cultured with the conditioned medium by Western blotting, and in the upper panel NGAL mRNA expression of HK-2 cells harvested at the indicated time points after addition of fresh medium (C) or medium supplemented with 1 ng/mL of IL-β (S).

The molecular forms of NGAL secreted by HK-2 cells were determined by Western blotting using mixed monoclonal antibodies (Mab697, Mab764 and Mab765) as detecting antibodies. The results shown in FIG. 10 (lower panel) indicate that the major form of NGAL secreted by HK-2 cells grown either in complete culture media or under stressful conditions in K-SFM or in media supplemented with cytokines (IL-β or TNF-α) or LPS is the monomeric form. The heterodimeric form of NGAL was also apparent after stimulation with IL-β whereas the dimeric form was absent in contrast to findings in supernatants of human neutrophils (FIG. 6). In FIG. 10, the mRNA levels of NGAL are shown in HK-2 cells after incubation with IL-β. The results show increased expression indicating active synthesis of NGAL by the HK-2 cells.

Discussion

NGAL was originally isolated from human neutrophils and it has been our previously shown that the measurement of NGAL in blood is a superior means to distinguish acute infections caused by bacteria or virus. Subsequent studies have found that NGAL may also be expressed in other cells such as in kidney, liver and epithelial tissue under certain conditions and that NGAL measurement in urine and plasma might serve as a biomarker of acute kidney injury. Example 1 shows that antibody configuration of an NGAL assay has an impact on the clinical performance of the assay. Several forms of NGAL were identified in urine of patients with AKI. This example further shows that the monomeric form and to some extent the heterodimeric forms are the predominant forms produced by tubular epithelial cells, whereas the dimeric form seems unique to the neutrophils (see FIG. 6). The monomeric form was also produced by neutrophils. One interesting finding in the present study is the differences in recognition of these different forms by the employed antibodies, since the monomeric and dimeric forms originating from neutrophils were identified by all monoclonal antibodies as well as by the polyclonal antibodies. This was contrasted by the almost complete inability of Mab697 to recognize these forms in urine. Also the Mab765 showed a strong reaction to these forms in neutrophil supernatants but only weak recognition of the dimeric form in urine. Without wishing to be bound by theory, it is believed that differences in epitope exposure of the different NGAL forms and thus differences in molecular structures are the cause.

The presence of different molecular forms of NGAL in urine and differences in epitope recognition of the antibodies were also reflected by the large differences in NGAL quantification in urine by the employed assays. Not only were the preoperative levels very different in spite of the same calibrator used in the assays, but also the relative changes after operation. It is apparent that the fold increases were highest with the ELISA that used either polyclonal antibodies alone or polyclonal antibodies in combination with either Mab764 or Mab 765. These two mabs were also those that recognized most forms in urine on Western blotting. However, the combination of these two mabs recognized less, which suggests that additional molecular forms were picked up by the polyclonal antibodies. From the gel filtration experiments, it seems as if these differences in recognition of various forms primarily are related to differences in recognition of the monomeric NGAL, since only one assay seemed to recognize the dimeric form differently. The differences could not be explained by overall analytical performances of the assays, since all showed similar sensitivities, imprecision, recovery, etc.

Based on fractional excretion of NGAL in humans (CN-GAL/CCr), in-situ hybridization in mice, and the fact that NGAL is an acute-phase protein, previous reports have claimed that NGAL accumulation in urine might derive from local renal synthesis, which comprises the major fraction of urinary NGAL, and distant organs and immune cells. Such conclusions, however, are weakened by several uncertainties related to kidney handling of NGAL in terms of glomerular filtration rate, tubular reabsorption, and urine dilution, but also to the fact that in-situ hybridization was performed in mice and that such techniques poorly reflect the capacity of cells to produce proteins. Our findings, however, indeed support the notion that human tubular epithelial cells have the capacity to produce NGAL, since the mRNA expression and protein production were induced by several conditions relevant to a kidney living under stressful or inflammatory conditions such as is seen during extracorporeal circulation. We found the cytokine IL-1R to be the most potent stimulus, which is compatible with the work of others using lung epithelial cell line. High levels of neutrophil secretory proteins and cytokines such as IL-β and TNF-α have been observed during and after cardiac surgery by many previous studies. The present results therefore demonstrate that NGAL is present in urine in many different forms and that assays for the quantification of NGAL in urine which account for this diversity are advantageous. Thus, in one embodiment, the invention is directed to an assay that preferentially identifies NGAL originating from the tubular epithelium, since the molecular structure of NGAL seems slightly different from the structure of NGAL from the neutrophils Such assays are therefore more specific and sensitive in the detection of AKI and of major benefit to patients at risk of developing impaired kidney function.

The methods, devices and kits of the present invention have been described with reference to specific embodiments and the Example demonstrates specific aspects of the invention. However, it will be appreciated that additional embodiments, aspects, variations and modifications of the invention can be effected by a person of ordinary skill in the art without departing from the scope of the invention as claimed.

What is claimed is:

1. A method for detecting acute kidney injury in a cardiac surgery patient, comprising
   (a) detecting an amount of homodimeric NGAL protein in urine samples from the patient prior to and at least one day after cardiac surgery by contacting a respective urine sample from the patient with a capturing antibody which binds monomeric, homodimeric and heterodimeric NGAL proteins and which is immobilized on a first enzyme-linked immunosorbent assay (ELISA) device to allow binding of NGAL proteins in the sample, and detecting bound homodimeric NGAL protein using a first detectable monoclonal antibody which specifically binds homodimeric NGAL protein,
   (b) detecting an amount of monomeric NGAL protein in the urine samples from the patient prior to and at least one day after cardiac surgery by contacting the respective urine sample from the patient with a capturing antibody which binds monomeric, homodimeric and heterodimeric NGAL proteins and which is immobilized on a second ELISA device to allow binding of NGAL proteins in the sample, and detecting bound monomeric NGAL protein using a second detectable monoclonal antibody which binds monomeric NGAL protein, and
   (c) comparing a first ratio of the detected amount of monomeric NGAL protein to homodimeric NGAL protein in the sample prior to cardiac surgery with a second ratio of the amount of detected monomeric NGAL protein to homodimeric NGAL protein in the sample at least one day after cardiac surgery,
   wherein, the second ratio being greater than the first ratio indicates the patient has suffered acute kidney injury and the second ratio being less than the first ratio indicates the patient has not suffered acute kidney injury.

2. The method according to claim 1, wherein the antibodies are produced from purified NGAL protein.

3. The method according to claim 1, wherein the capturing antibody which binds monomeric, homodimeric and heterodimeric NGAL proteins in step (a) is a monoclonal antibody.

4. The method according to claim 1, wherein the capturing antibody which binds monomeric, homodimeric and heterodimeric NGAL proteins in step (b) is a monoclonal antibody.

5. A method for detecting NGAL protein originating from kidney in a cardiac surgery patient urine sample, comprising
   (a) providing urine samples from the patient prior to and at least one day after cardiac surgery,
   (b) detecting an amount of homodimeric NGAL protein in the urine samples from the patient prior to and at least one day after cardiac surgery by contacting a respective urine sample from the patient with a capturing antibody which binds monomeric, homodimeric and heterodimeric NGAL proteins and which is immobilized on a first enzyme-linked immunosorbent assay (ELISA) device to allow binding of NGAL proteins in the sample, and detecting bound homodimeric NGAL protein using a first detectable monoclonal antibody which specifically binds homodimeric NGAL protein, and
   (c) detecting an amount of monomeric NGAL protein in the urine samples from the patient prior to and at least one day after cardiac surgery by contacting the respective urine sample from the patient with a capturing antibody which binds monomeric, homodimeric and heterodimeric NGAL proteins and which is immobilized on a second ELISA device to allow binding of NGAL proteins in the sample, and detecting bound monomeric NGAL protein using a second detectable monoclonal antibody which binds monomeric NGAL protein,
   wherein an increase of the ratio of the detected amount of monomeric NGAL protein to homodimeric NGAL protein in the sample at least one day after cardiac surgery over the ratio of the amount of detected monomeric NGAL protein to homodimeric NGAL protein in the sample prior to cardiac surgery indicates the NGAL protein origin is from kidney.

6. The method according to claim 5, wherein the antibodies are produced from purified NGAL protein.

7. The method according to claim 5, wherein the capturing antibody which binds monomeric, homodimeric and heterodimeric NGAL proteins in step (b) is a monoclonal antibody.

8. The method according to claim 5, wherein the capturing antibody which binds monomeric, homodimeric and heterodimeric NGAL proteins in step (c) is a monoclonal antibody.

9. A method for detecting NGAL protein in a cardiac surgery patient urine sample, comprising
   (a) providing urine samples from the patient prior to and at least one day after cardiac surgery,
   (b) detecting an amount of homodimeric NGAL protein in the urine samples from the patient prior to and at least one day after cardiac surgery by contacting a respective urine sample from the patient with a capturing antibody which binds monomeric, homodimeric and heterodimeric NGAL proteins and which is immobilized on a first enzyme-linked immunosorbent assay (ELISA) device to allow binding of NGAL proteins in the sample, and detecting bound homodimeric NGAL protein using a first detectable monoclonal antibody which specifically binds homodimeric NGAL protein, and
   (c) detecting an amount of monomeric NGAL protein in the urine samples from the patient prior to and at least one day after cardiac surgery by contacting the respective urine sample from the patient with a capturing antibody which binds monomeric, homodimeric and heterodimeric NGAL proteins and which is immobilized on a second ELISA device to allow binding of NGAL proteins in the sample, and detecting bound monomeric NGAL protein using a second detectable monoclonal antibody which binds monomeric NGAL protein.

10. The method according to claim 9, wherein the antibodies are produced from purified NGAL protein.

11. The method according to claim 9, wherein the capturing antibody which binds monomeric, homodimeric and heterodimeric NGAL proteins in step (b) is a monoclonal antibody.

12. The method according to claim 9, wherein the capturing antibody which binds monomeric, homodimeric and heterodimeric NGAL proteins in step (c) is a monoclonal antibody.

\* \* \* \* \*